United States Patent

Sklebitz et al.

[11] Patent Number: 6,064,715
[45] Date of Patent: May 16, 2000

[54] X-RAY EXPOSURE APPARATUS FOR DIGITAL MAMMOGRAPHY

[75] Inventors: Hartmut Sklebitz, Erlangen; Tom Weidner, Nuremberg, both of Germany

[73] Assignee: Siemens Aktiengesellschaft, Munich, Germany

[21] Appl. No.: 09/093,344

[22] Filed: Jun. 9, 1998

[30] Foreign Application Priority Data

Jul. 21, 1997 [DE] Germany ............ 197 312 35

[51] Int. Cl.$^7$ .................................... A61B 6/04
[52] U.S. Cl. ............................. 378/37; 378/983
[58] Field of Search ...................... 378/37, 98.3

[56] References Cited

U.S. PATENT DOCUMENTS

| | | | |
|---|---|---|---|
| 4,821,727 | 4/1989 | Levene et al. | 600/407 |
| 5,235,191 | 8/1993 | Miller | 250/486.1 |
| 5,247,555 | 9/1993 | Moore et al. | 378/4 |
| 5,365,562 | 11/1994 | Toker | 378/37 |
| 5,712,890 | 1/1998 | Spivey et al. | 378/37 |
| 5,723,865 | 3/1998 | Trissel et al. | 250/368 |
| 5,790,629 | 8/1998 | Svensson et al. | 378/98.7 |

FOREIGN PATENT DOCUMENTS 41 38 659  5/1992  Germany.
196 00 577  7/1997  Germany.

OTHER PUBLICATIONS

CCD Mosaic Technique for Large–Field Digital Mammography—Jalink et al—IEEE Trans. On Med. Imaging, vol. 15, No. 3, Jun. 1996.

*Primary Examiner*—David P. Porta
*Assistant Examiner*—Allen C. Ho
*Attorney, Agent, or Firm*—Hill & Simpson

[57] ABSTRACT

An X-Ray exposure apparatus for digital mammography allows an exposure of the entire breast to be obtained with a single solid state detector. To this end, an apparatus housing is provided has an acute angle at the patient side, with a device for the deflection of the image from a luminescent screen and optics for imaging this image on the solid state detector are arranged at this side. The solid state detector is arranged at the patient-remote side of the X-ray exposure apparatus.

3 Claims, 1 Drawing Sheet

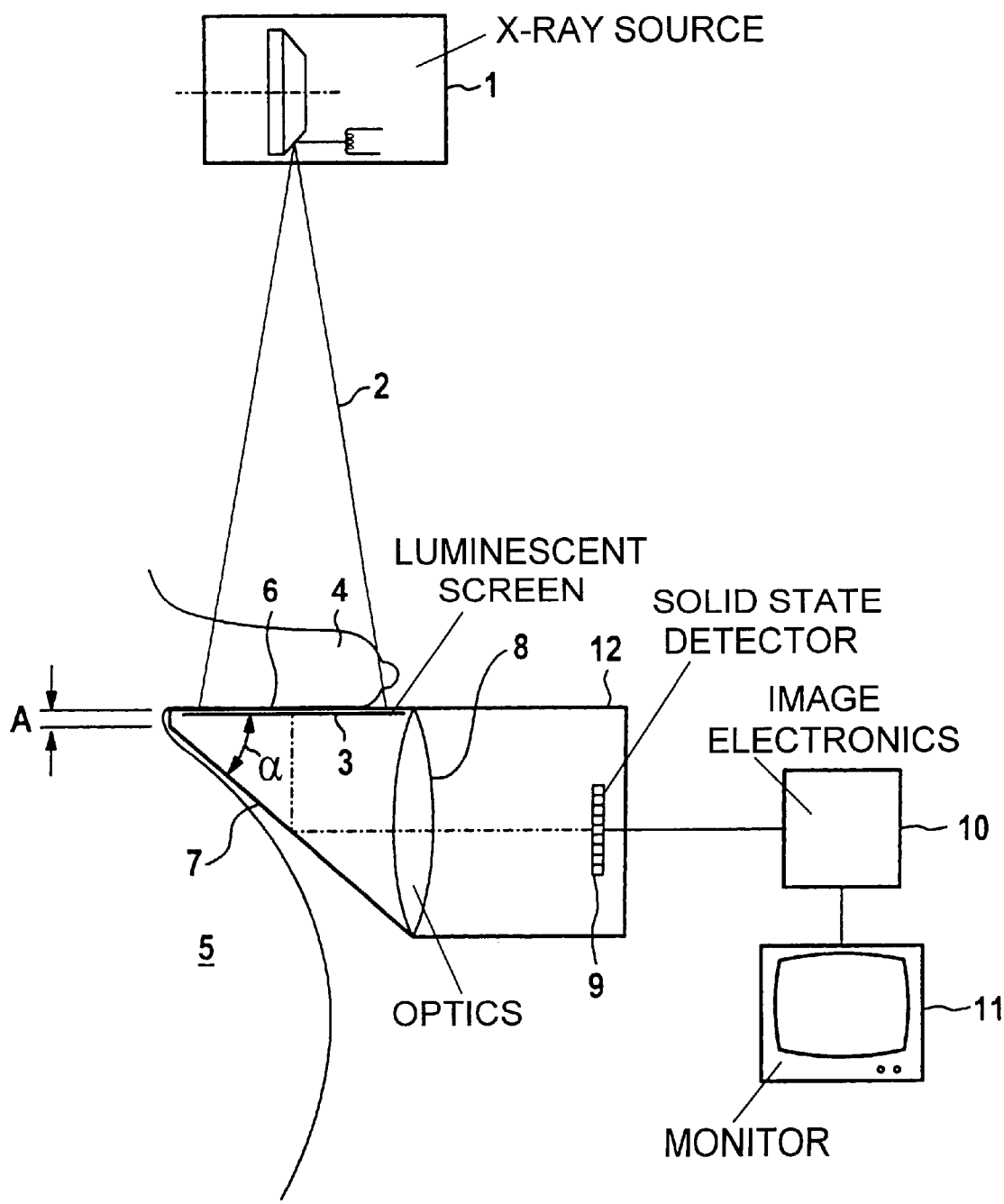

X-RAY EXPOSURE APPARATUS FOR DIGITAL MAMMOGRAPHY

BACKGROUND OF THE INVENTION

1. Field of the Invention

The present invention is directed to an X-ray exposure apparatus of the type suited for use in digital mammography.

2. Description of the Prior Art

X-ray exposure apparatuses are known wherein the X-ray image is imaged from a luminescent screen onto an image plane with the assistance of an optical system. The luminescent screen, for example, can be the output screen of an X-ray image intensifier, and the image plane can lie in a video camera. Instead of an X-ray image intensifier, solid state image converters have recently come into use in radiology, these being composed of a matrix of detector elements whose electrical output signals are supplied to an image computer for generating an X-ray image. The luminescent screen converts the X-rays into visible light, and the solid state converter converts the visible light into corresponding electrical signals. Such a detector can, for example, be a CCD converter or a converter on the basis of amorphous, hydrated silicon.

Solid state detectors cannot yet be implemented with a size such that they can be arranged immediately behind the luminescent screen for picking up the entire X-ray image. It is therefore known to prepare digital mammography exposures with the assistance of a mosaic of solid state detectors that is shifted for filling out the interspaces between the individual detectors (IEEE Transactions on Medical Imaging, Vol. 15, No. 3, Jun. 1996, pages 260 through 267).

German OS 196 00 577 discloses a device for positioning a female breast so that it has a stable shape for diagnosis and therapy, wherein an approximately hemispherical, position-fixable receptacle shell for the breast is provided, with sensors or radiation sources being arranged around this shell. This device is primarily suitable for ultrasound image generation and for therapy. No means are provided for X-ray exposures.

German OS 41 38 659 discloses a medical X-ray image pickup system, particularly for dental exposures, wherein a strip-shaped X-ray fluorescent screen is provided from which optical fibers are conducted to solid state image pickup devices, the latter being curved. This apparatus is not suitable for the production of mammographic exposures.

SUMMARY OF THE INVENTION

An object of the present invention is to provide an X-ray exposure apparatus of the type initially cited wherein a digital X-ray exposure of even relatively adipose female patients can be easily produced with the assistance of a single solid state detector having relatively small dimensions.

The above object is achieved in accordance with the principles of the present invention in an X-ray exposure apparatus for digital mammography having a housing with an acute angle at a side of the housing intended to face toward the patient in order to receive a female breast at a breast seating surface, the housing having a luminescent screen disposed behind the breast seating surface, with light emission from the luminescent screen being deflected by approximately 90° and being imaged, via optics, onto a solid-state detector disposed at a side of the housing facing away from the patient side of the housing.

With the inventive X-ray exposure apparatus, an exposure of the entire adipose breast is easily possible with using only one solid state detector. The inventive X-ray exposure apparatus is basically a camera with angular optics that adapts excellently to the anatomy of adipose female patients.

DESCRIPTION OF THE DRAWINGS

The single Figure is a schematic illustration of an X-ray exposure apparatus for digital mammography, constructed and operating in accordance with the principles of the present invention.

DESCRIPTION OF THE PREFERRED EMBODIMENTS

The drawing shows an X-ray source 1 which emits an X-ray beam 2 that strikes a luminescent screen 3 after it has penetrated the breast 4 of a female patient 5. The luminescent screen is arranged behind a seating surface 6. The light emission of the luminescent screen 3 is conducted through an optics 8 onto a solid state detector 9 by a mirror 7 inclined by approximately 45° relative to the seating surface 6, i.e. is deflected by approximately 90°. The output signals of the solid state detector 9 are supplied to image electronics 10 that generates an image of the breast 4 therefrom, this being reproduced on a monitor 11.

It is important that the X-ray exposure apparatus exhibits an acute angle $\alpha$ at its side facing toward the female patient 5, and that the mirror 7 is arranged at that side facing away from the female patient 5. As shown in the drawing, adipose female patients can thus also be examined well. It is also important that the spacing A between the left upper end of the mirror 7, in general the upper left end of the beam deflection device, and the seating surface 6 is as small as possible. The spacing A lies in the range of millimeters up to a few centimeters, such as between about 5 millimeters and about 5 centimeters. As a result thereof, a good approach of the X-ray exposure apparatus to the patient 5 is enabled.

The luminescent screen 3 is preferably composed of CsI: Tl, which is generated in needle structures by vapor deposition. Such a screen also enables good transfer function in that case wherein the light leaves the phosphor opposite the X-radiation entry side.

The optics 8 can be, as illustrated, a combination mirror-lens optics, or as a prism optics system can be employed. A high light intensity is important, so that no quanta bottleneck arises.

The image sensor, i.e. the solid state detector 9, is preferably a solid state detector of crystalline silicon (for example, CCDs, CMOS sensors with active pixels). Cooling the image sensor (for example, with a Peltier element) is recommended for improving the dark current behavior. It can be advantageous for the camera housing to be moisture-tight because no water vapor can then form on the CCD.

The drawing also shows the housing 12 of the X-ray exposure apparatus that, of course, likewise exhibits an acute angle at that side facing toward the patient 5, corresponding to the inclination of the mirror 7.

Although various minor modifications might be suggested by those skilled in the art, it should be understood that our wish to embody within the scope of the patent warranted hereon all such modifications as reasonably and properly come with the scope of our contribution to the art.

We claim as our invention:

1. An X-ray exposure apparatus for digital mammography comprising:

a housing having a first side adapted to face toward a patient during an examination and having a second side opposite said first side, and said housing having a breast seating surface adapted to receive a female breast thereon, said first side and said breast seating surface being disposed at said housing at an acute angle relative to each other;

an X-ray source which emits an X-ray beam which irradiates said breast seating surface;

a luminescent screen disposed in said housing behind said breast seating surface on which X-rays in said X-ray beam are incident after passing through said breast seating surface, said luminescent screen producing light emission dependent on the X-rays incident thereon;

means contained in said housing for deflecting said light emission from said luminescent screen by approximately 90° to produce deflected light emission;

a solid state detector disposed at said second side of said housing; and optics means in said housing for imaging said deflected light emission onto said solid state detector.

2. An apparatus as claimed in claim 1 wherein said means for deflecting comprises a mirror disposed at said acute angle at said first side of said housing.

3. An apparatus as claimed in claim 2 wherein said mirror has a mirror end facing toward said first side of said housing, and wherein said mirror end is spaced from said seating surface at a spacing in a range between about 5 millimeters and about 5 centimeters.

* * * * *